United States Patent [19]
Ostermaier

[11] Patent Number: 5,961,788
[45] Date of Patent: Oct. 5, 1999

[54] SEQUENTIAL DISTILLATION PROCESS FOR REMOVING TETRAHYDROAZEPINE FROM AMINOCAPRONITRILE AND/OR HEXAMETHYLENEDIAMINE

[75] Inventor: John Joseph Ostermaier, Wilmington, Del.

[73] Assignee: E. I. du Pont de Nemours and Company, Wilmington, Del.

[21] Appl. No.: 09/169,522

[22] Filed: Oct. 9, 1998

[51] Int. Cl.⁶ ............................ B01D 3/34; C07C 209/82
[52] U.S. Cl. .................. 203/37; 203/78; 203/80; 558/452; 558/456; 564/498
[58] Field of Search ............................ 203/37, 3, DIG. 9, 203/78, 91, 80, 29, DIG. 16; 558/452, 456, 463; 564/498, 497, 492

[56] References Cited

U.S. PATENT DOCUMENTS

| | | | |
|---|---|---|---|
| 4,282,381 | 8/1981 | Buehler et al. | 568/498 |
| 5,133,838 | 7/1992 | Sieja | 203/29 |
| 5,153,351 | 10/1992 | Sieja | 558/452 |
| 5,162,567 | 11/1992 | Sieja | 558/452 |
| 5,192,399 | 3/1993 | Sieja | 203/37 |

*Primary Examiner*—Virginia Manoharan

[57] ABSTRACT

A process for removing tetrahydroazepine from aminocapronitrile or hexamethylenediamine by sequential distillation in which the overhead from the second distillation is combined with a fresh, incoming mixture of tetrahydroazepine and aminocapronitrile or hexamethylenediamine.

11 Claims, 1 Drawing Sheet

SEQUENTIAL DISTILLATION PROCESS FOR REMOVING TETRAHYDROAZEPINE FROM AMINOCAPRONITRILE AND/OR HEXAMETHYLENEDIAMINE

BACKGROUND OF THE INVENTION

Tetrahydroazepine (THA) is an impurity that is formed when adiponitrile (ADN) is hydrogenated to give aminocapronitrile (ACN) and hexamethylenediamine (HMD). THA is an undesirable impurity, because it causes branching and color in Nylon 6 and Nylon 66 polymer. THA can be removed from ACN and HMD by distillation in the presence of a strong base, such as sodium hydroxide. The strong base is believed to catalyze the reaction of the THA with either ACN or HMD to form high boiling THA-containing oligomers that are easily removed from the ACN and/or HMD by distilling the ACN or HMD overhead and leaving the THA-containing high boiling oligomers as distillation bottoms. See U.S. Pat. No. 5,192,399.

According to U.S. Pat. No. 5,192,399, ACN or HMD contaminated with THA may be fed to a distillation apparatus (a single-stage flasher), along with an aqueous caustic solution. Product ACN or HMD, considerably reduced in THA content, is taken overhead, and the THA-containing oligomers are removed with the bottoms from the distillation. A single, multi-stage distillation column may be employed, but it is not necessary.

The type of distillation process described above is capable of achieving maximum ACN yields of only about 85%. While the exact chemical theory explaining this yield limitation is not well understood, it is believed that as ACN is distilled from the THA/ACN mixture, the THA/ACN oligomer is broken down, causing more THA to be taken overhead, thus contaminating the ACN or HMD product. Thus, attempts to recover more ACN and/or HMD inevitably result in an increase in THA content in the ACN or HMD product.

It would be desirable to have a process for removing THA from ACN and/or HMD to produce ACN and/or HMD in yields higher than about 85% while maintaining low THA content.

BRIEF DESCRIPTION OF THE DRAWING

The drawing consists of one FIGURE showing a block diagram illustrating the process of the present invention.

SUMMARY OF THE INVENTION

Figure 1:
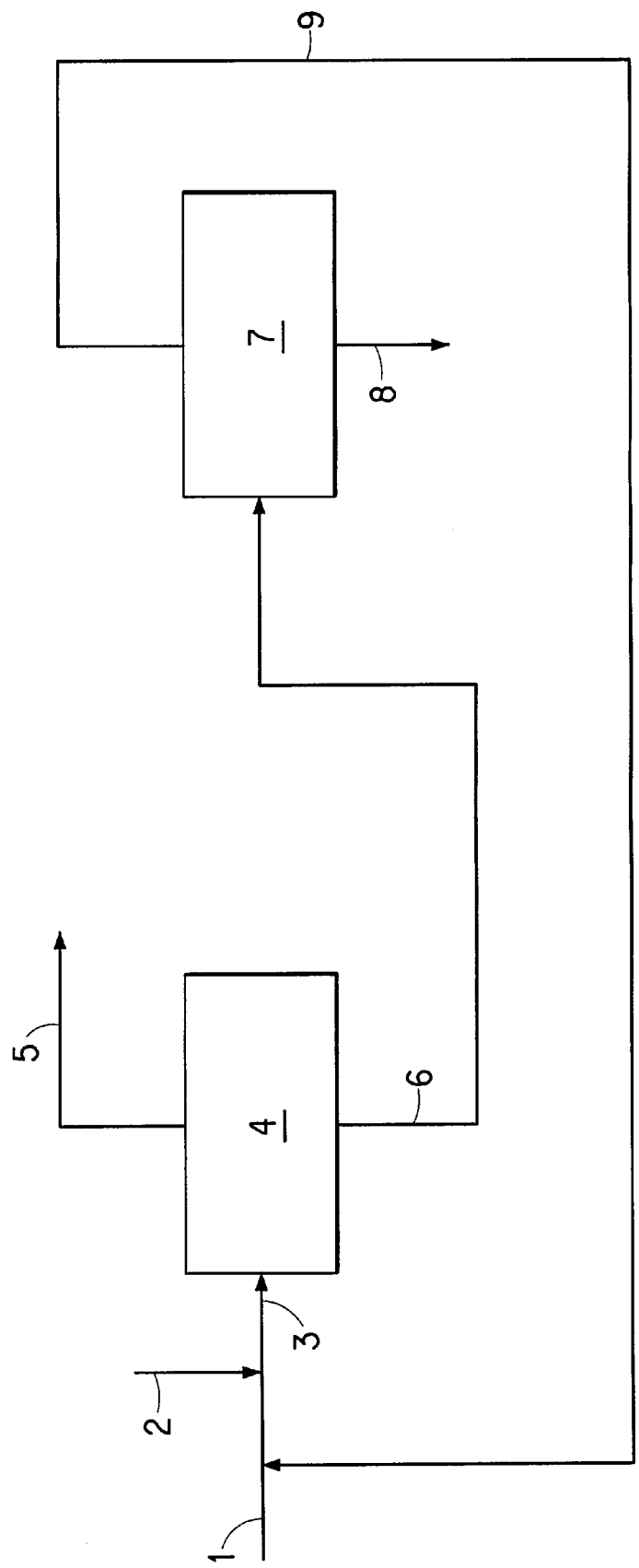

The present invention is a process for separating a compound selected from the group consisting of aminocapronitrile and hexamethylenediamine from a mixture comprising the compound and tetrahydroazepine, said process comprising:

(1) distilling a feed comprising (i) a compound selected from the group consisting of hexamethylenediamine and aminocapronitrile, and (ii) tetrahydroazepine, in the presence of a caustic compound to form (a) a first distillate comprising a major portion of the compound of the feed and a minor portion of the tetrahydroazepine and (b) a first bottoms comprising the remainder of the tetrahydroazepine in the feed;

(2) distilling the first bottoms to form a second distillate and a second bottoms;

(3) combining the second distillate with the compound and tetrahydroazepine to form the feed of step (1); and (4) collecting the first distillate which comprises the compound and the minor portion of the tetrahydroazepine;

wherein the mass flow ratio of first distillate to feed is between 0.5 and 0.95 and the mass flow ratio of second distillate to first bottoms is between 0.5 and 0.95.

This process permits aminocapronitrile or hexamethylenediamine with low THA content to be recovered with yields as high as about 98%.

DETAILED DESCRIPTION

The present process utilizes at least two distillation units to produce ACN and/or HMD from an ACN or HMD material which also contains THA.

Referring now to FIG. 1, an incoming stream 1 comprising ACN (and/or HMD) and THA is mixed with second distillate 9 and caustic compound 2 to produce a feed 3 of ACN (and/or HMD), THA and caustic compound. Feed 3 is fed to a distillation apparatus 4 where there is produced a first distillate 5, containing ACN (and/or HMD), substantially reduced in THA. There is also produced a first bottoms 6, high in THA content, which is fed to distillation apparatus 7. In distillation apparatus 7, first bottoms 6 is separated into second bottoms 8 (high in THA) and second distillate 9, the latter being recycled and combined with incoming stream 1. Further distillation units may be employed in similar configuration.

It has been found that when the first bottoms 6 is distilled again in distillation apparatus 7, second distillate 9 has a higher THA content than that of first distillate 5, but that second distillate 9 is suitable for blending with incoming stream 1 for feeding to distillation apparatus 4. This two-unit distillation allows the recovery of low THA-containing ACN and/or HMD product (first distillate) to be increased above that which is achievable in a single unit distillation. ACN and/or HMD materials containing very high THA content may require more than two distillation units to produce high yields of low THA-containing ACN and/or HMD product.

It has been found that the amount of THA present in first distillate 5 is highly dependent on the distillate product 5 to feed 3 mass flow ratio, as well as on the second distillate 9 to first bottoms 6 mass flow ratio. As these ratios increase the amount of THA present in first distillate 5 increases. In the limit of these ratios equaling 1.0, there is no THA removal, and the THA content of first distillate 5 is the same as that of the feed. As these ratios are reduced below 1.0, the amount of THA in first distillate 5 decreases. Ratios between 0.5 and 0.95 are desirable, with ratios between 0.7 and 0.9 being more desirable. Mass flow ratios can be controlled by adjusting the amount of heat input to distillation apparatus 4 and distillation apparatus 7.

The concentration of caustic compound in the feed 3 also is an important variable. Suitable caustic compounds include a variety of bases such as alkali metal hydroxides, some alkaline earth hydroxides, tetraalkylammonium hydroxide, alkali metal alkoxides and alkaline earth metal alkoxides. Specific bases include sodium hydroxide, potassium hydroxide, lithium hydroxide, barium hydroxide, tetra butyl ammonium hydroxide, sodium methoxide, potassium ethoxide and potassium tert-butoxide. It has been found that below about 10 ppm caustic compound, the THA is not effectively removed, and above 2500 ppm caustic compound secondary reactions occur that form organic solids. The preferred concentration of caustic compound in the feed 3 is above 10 ppm, but below 1000 ppm, and a more preferred range is between 100 ppm and 300 ppm. Higher levels of caustic compound cause the following undesirable problems:

1. plugging of tails lines;
2. organic solids formation in tails;
3. increased frothing or foaming;
4. increased difficulty or recovering ACN from the tails purge; and
5. increased ingredients and waste disposal costs.

It has been found that caustic must be introduced in distillation apparatus 4 at the bottom of the column. Introduction elsewhere has not been found to be effective.

It is known that the oligomer products formed in this process are thermally unstable, and will decompose to re-form THA if excessive temperatures exist in the distillation. It has been found that below 150° C. the concentration of THA in the first distillate 5 is essentially constant, but above this temperature the amount of THA in first distillate increases. Temperatures above 150° C. can be employed, but are progressively less desirable as they increase.

The hold-up times of first bottoms 6 in distillation apparatus 4 and of second bottoms 8 in distillation apparatus 7 are other important variables. Since distillation apparatus 4 and distillation apparatus 7 are preferably single stage flash drums, which are essentially back-mixed chemical reactors, the extent of any chemical reactions that occur will increase as the hold up times increase. As stated previously, the oligomers formed in this process are thermally unstable and decompose to re-form THA when heated. The extent of this decomposition to re-form THA increases as the hold up times in both first distillation apparatus 4 and second distillation apparatus 7 increase. It is therefore desirable to keep the hold up times as short as practical. Desirable hold-up times are less than 1 hour when the temperature is kept below 150° C.

The process of the present invention may be performed in either a batch or continuous mode.

The present invention is illustrated by the following non-limiting examples.

EXAMPLES

Comparative Example—Effect of Distillate to Feed Mass Flow Ratio on THA Removal from ACN Using Single Unit Distillation ACN containing 745 ppm THA and about 200 ppm sodium hydroxide was continuously distilled in a laboratory distillation apparatus at a temperature of 132° C. The laboratory distillation apparatus consisted of a one-liter round bottom flask which was heated with an electric heating mantle, a two inch diameter vacuum jacketed column containing 5 Olderschaw plates, a water cooled condenser, and a magnetically operated splitter head to allow adjustment of reflux ratio. ACN containing 745 ppm THA was fed continuously to the column reboiler through a tee connector using a laboratory positive displacement pump. Caustic was fed to the tee connector as a 10% aqueous solution using a syringe pump. Distillate to feed ratios were set by measuring the flow rate of distillate, and adjusting the feed rate to give the desired ratio. A bottoms purge was withdrawn from the column reboiler to maintain constant level in the reboiler. The distillations were carried out at the distillate to feed mass flow ratios indicated below. The ACN product was distilled overhead and analyzed for THA content.

| RATIO | (YIELD) | PPM THA IN DISTILLATE |
|-------|---------|------------------------|
| 1.0   | (100%)  | 745                    |
| 0.9   | ( 90%)  | 32                     |
| 0.8   | ( 80%)  | 20                     |
| 0.7   | ( 70%)  | 8                      |

These data clearly indicate that the amount of THA in the distilled ACN product decreases as the distillate to feed mass flow ratio decreases.

Example—Removal of THA from ACN by Sequential Distillation

This example demonstrates that by using sequential distillation it is possible to distill THA-containing ACN to obtain a high yield of ACN product that contains low amounts of THA. THA-containing ACN was distilled in a commercial scale distillation apparatus to give a bottoms which was collected. A laboratory scale distillation apparatus was then used to distill the collected bottoms. The distillate from this laboratory scale distillation apparatus was then collected. The collected distillate was then blended with more of the original THA-containing ACN, and this blended material was then distilled using the laboratory scale distillation apparatus for a second time. The distillate from this second use of the laboratory scale distillation apparatus was the product of the present process and was analyzed for ACN and THA.

The laboratory distillation apparatus consisted of a one-liter round bottom flask which was heated with an electric heating mantle, a two inch diameter vacuum jacketed column containing 10 inches of 0.5 inch Raschig rings, a water cooled condenser, and a magnetically operated splitter head to allow adjustment of reflux ratio. The various feed materials were fed continuously to the column reboiler using a laboratory positive displacement pump. Caustic was fed as a 10% aqueous solution using a syringe pump. Distillate to feed ratios were set by measuring the flow rate of distillate, and adjusting the feed rate to give the desired ratio. A bottoms purge was withdrawn from the column reboiler to maintain constant level in the reboiler.

ACN containing 745 ppm THA was fed to the commercial scale distillation apparatus together with 10% caustic solution at rates to provide a blended feed stream containing ACN, 300 ppm caustic and about 745 ppm THA. The mass flow ratio of distillate to feed was 0.7. The top of the distillation apparatus was operated at a pressure of 20 mm Hg and a temperature of 125° C. A high THA-containing bottoms was collected for the next step in the sequential distillation.

The collected bottoms from the above-described commercial scale distillation were fed to the laboratory scale distillation apparatus without additional caustic. The mass flow ratio of distillate to feed was 0.90. The top of the distillation apparatus was operated at a pressure of 10 mm Hg and a temperature of 110° C. The distillate, containing 990 ppm THA, was collected. The distillate was blended with fresh ACN containing 745 ppm THA (the same material that was fed to the commercial scale distillation apparatus) and 10% aqueous sodium hydroxide to provide a feed stream that contained ACN and about 200 ppm sodium hydroxide and 830 ppm THA. This stream was fed to the reboiler of the distillation apparatus. The mass flow ratio of distillate to feed was 0.8. The top of the distillation apparatus was operated at a pressure of 20 mm Hg and a temperature of 125° C. The distilled product was ACN which contained only 20 ppm THA.

The above process gave an overall ACN recovery of 97% with a THA content of 20 ppm. By comparison, a single step distillation process that produces ACN containing 20 ppm THA requires a distillate to feed ratio of 0.8, which gives only an 80% recovery of ACN, as illustrated in the Comparative Example.

What is claimed is:

1. A process for separating a compound selected from the group consisting of aminocapronitrile and hexamethylenediamine from a mixture comprising the compound and tetrahydroazepine, said process comprising (1) distilling a feed comprising (i) a compound selected from the group consisting of hexamethylenediamine and aminocapronitrile, and (ii) tetrahydroazepine, in the presence of a caustic compound to form (a) a first distillate comprising a major portion of the compound of the feed and a minor portion of the tetrahydroazepine and (b) a first bottoms comprising the remainder of the tetrahydroazepine in the feed;

(2) distilling the first bottoms to form a second distillate and a second bottoms;

(3) combining the second distillate with the compound (i) and tetrahydroazepine (ii) to form the feed of step (1); and (4) collecting the first distillate which comprises the major portion of the compound and the minor portion of the tetrahydroazepine;

wherein the mass flow ratio of first distillate to feed is between 0.5 and 0.95 and the mass flow ratio of second distillate to first bottoms is between 0.5 and 0.95, provided that when step (1) is carried out in a distillation column, the caustic chemical is introduced at the bottom of the column.

2. The process of claim 1 in which the compound is aminocapronitrile.

3. The process of claim 2 in which the ratios are between 0.7 and 0.9.

4. The process of claim 3 in which the caustic compound is present at a concentration of between 10 ppm and 1000 ppm.

5. The process of claim 4 in which the concentration is between 100 and 300 ppm.

6. The process of claim 5 in which the caustic compound is sodium hydroxide.

7. The process of claim 1 in which the compound (i) is hexamethylenediamine.

8. The process of claim 7 in which the ratios are between 0.7 and 0.9.

9. The process of claim 8 in which the caustic compound is present at a concentration of between 10 ppm and 1000 ppm.

10. The process of claim 9 in which the concentration is between 100 and 300 ppm.

11. The process of claim 10 in which the caustic compound is sodium hydroxide.

* * * * *